United States Patent [19]

Leeson et al.

[11] Patent Number: 4,863,953
[45] Date of Patent: Sep. 5, 1989

[54] [3R]-3-AMINO-1-HYDROXY PYRROLIDIN-2-ONE AND ITS USE AS A NEUROPROTECTIVE AGENT

[75] Inventors: Paul D. Leeson, Cambridge; Brian J. Williams, Great Dunmow, both of England

[73] Assignee: Merck & Co., Inc., Rahway, N.J.

[21] Appl. No.: 273,392

[22] Filed: Nov. 18, 1988

[30] Foreign Application Priority Data

Nov. 27, 1987 [GB] United Kingdom ............... 8727792

[51] Int. Cl.⁴ ................ C07D 207/273; A61K 31/40
[52] U.S. Cl. .................................... 514/425; 548/542
[58] Field of Search ...................... 548/542; 514/425

[56] References Cited

FOREIGN PATENT DOCUMENTS 1041861 9/1966 United Kingdom .

OTHER PUBLICATIONS

Evans et al., Brain Research, 1978, 148, 536-542.
Barlos et al [C.A., 110(5):39341b] Liebigs Ann. Chem. (12) 1127-33 (1988).
Olverman [CA 109(19):163649b] Neuroscience (Oxford), 26 (1) 17-31 1988.
Foster et al [C.A., 96(17) 136522m]Br. J. Pharm., 74(3) 723-9 (1981).
Dimoto et al [CA 95(7):57583h] J. Biol. Chem., 256(10), 5134-43 (1981).

Primary Examiner—David B. Springer
Attorney, Agent, or Firm—William H. Nicholson; Joseph F. DiPrima

[57] ABSTRACT

The present invention provides R(+)-3-amino-1-hydroxypyrrolidin-2-one of formula I:

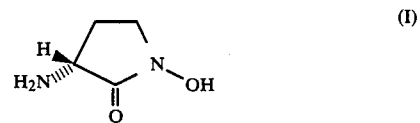

or pharmaceutically acceptable acid addition salt thereof, which compound is useful as an anticonvulsant agent and in the treatment and/or prevention of neurodegenerative disorders.

5 Claims, No Drawings

[3R]-3-AMINO-1-HYDROXY PYRROLIDIN-2-ONE AND ITS USE AS A NEUROPROTECTIVE AGENT

This invention relates to amino pyrrolidones which are specific antagonists of N-methyl-D-aspartate (NMDA) receptors and are therefore useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Olivo-ponto-cerebellar atrophy, anoxia such as from drowning, spinal cord and head injury and poisoning by exogenous NMDA poisons. The compounds are also useful as anticonvulsant agents.

The compound 3-amino-1-hydroxypyrrolidin-2-one is disclosed in Coll. Czech. Chem. Comm., 1959, 24, 1672 and its use in the treatment of epilepsy and Parkinson's disease is described in British Pat. No. 1,041,861. That compound, known as HA-966, has also been described as being able to antagonise selectively NMDA-induced excitation (Evans et al., Brain Research, 1978, 148, 536–542). Although such activity would suggest utility as a neuroprotective agent, the compound also demonstrates muscle relaxation and ataxia effects. These effects would be unacceptable in a therapeutic agent to be used chronically for the treatment of neurodegenerative diseases, since motor skills required for everyday living would be severely impaired.

It has now been found that the optical isomers of HA-966 can be prepared and, surprisingly, that the NMDA receptor antagonist activity is present in the R(+) isomer, whereas the undesirable ataxic side-effects are confined to the S(−) isomer. This unexpected dissociation of properties has enabled a therapeutically useful agent to be produced.

Accordingly, the present invention provides the R(+) isomer of 3-amino-1-hydroxypyrrolidin-2-one, having the structure and absolute stereochemistry as shown in formula I:

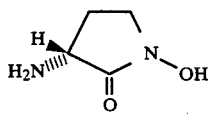
(I)

or a pharmaceutically acceptable acid addition salt thereof.

Suitable acid addition salts of compound I include pharmaceutically acceptable inorganic salts such as sulphate, nitrate, phosphate, borate, hydrochloride and hydrobromide, and pharmaceutically acceptable organic acid addition salts such as acetate, tartrate, maleate, citrate, succinate, benzoate, ascorbate, methanesulphonate, $\alpha$-ketoglutarate, $\alpha$-glycerophosphate and glucose-1-phosphate. Preferably the acid addition salt is a hemisuccinate, hydrochloride, $\alpha$-ketoglutarate, $\alpha$-glycerophosphate or glucose-1-phosphate, in particular the hydrochloride salt.

In order to achieve the advantageous separation of undesirable properties from useful neuroprotective activity, it is not necessary to exclude the S(−) isomer completely. Mixtures of isomers comprising at least 75% of the R(+) isomer of 3-amino-1-hydroxypyrrolidin-2-one may also be employed. Suitably, such enriched mixtures of isomers comprise at least 85%, especially at least 95%, of the (+) isomer, compound I. Preferably, the product of this invention comprises at least 99% of the R(+) isomer.

The novel compound of this invention may be prepared by resolution of racemic 3-amino-1-hydroxypyrrolidin-2-one. Known methods of resolution may be employed, for example comprising the formation and separation of diastereoisomers. Suitable resolving agents include chiral acids which form acid addition salts with the 3-amino group. Suitable resolving acids are camphor derivatives, such as camphor-10-sulphonic acid, $\alpha$-bromo-camphor-$\pi$-sulphonic acid, hydroxymethylene camphor and camphoric acid; menthol derivatives such as menthoxyacetic acid; naturally occurring optically active forms of tartaric acid and malic acid; and diacetyltartaric acid.

Alternatively, a chiral amino acid derivative may be employed in the resolution process, to form an amide bond which subsequently may be cleaved under mild conditions. A suitable amino acid which may be employed is L-phenylalanine, optionally having its amino group protected. The hydroxy group in 3-amino-1-hydroxypyrrolidin-2-one may also be reacted with the amino acid resolving agent.

The diastereoisomers are separated by conventional methods, such as chromatography or crystallisation. Suitable solvents for chromatography include ethyl acetate and petroleum ethers. Suitable solvents for crystallisation include non-polar solvents such as ether, methylene dichloride, petroleum ethers and methanol.

After separation, the R diastereoisomer is converted to R(+)-3-amino-1-hydroxypyrrolidin-2-one. If necessary the unwanted S(−) isomer may be reracemised for further resolution.

Alternatively, a protected derivative of 3-amino-1-hydroxypyrrolidin-2-one may be resolved using the methods described above.

The compound of this invention may also be prepared by a chiral process which comprises the cyclisation of a compound of formula II:

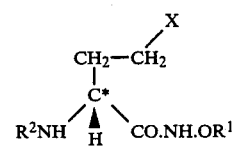
(II)

in which the carbon atom marked * is in the R configuration and wherein X represents a leaving group, $R^1$ represents hydrogen or a hydroxy protecting group, and $R^2$ represents hydrogen or an amino protecting group; and subsequently if necessary removing any protecting groups.

The leaving group X may be halogen, for example chloro, bromo or iodo; a sulphonyloxy group, such as methanesulphonyloxy, benzenesulphonyloxy or p-toluenesulphonyloxy; or a positively charged sulphur or phosphorus moiety.

A preferred group X is a moiety of formula $-S^+(CH_3)R$, wherein R represents aryl, alkyl or aralkyl, such as benzyl or $C_{1-3}$ alkyl. The compound II wherein X represents $-S^+(CH_3)R$ may be conveniently prepared in situ by alkylation of a compound of formula II wherein X represents methylthio. In that case, the alkylation may be carried out in the same reaction vessel as the cyclisation treatment. Preferred alkylating agents include benzyl bromide and methyl iodide.

Another suitable group X is triphenylphosphoniumoxy, —O—P+Ph$_3$. The compound of formula II wherein X represents —O—P+Ph$_3$ may be prepared by reacting the corresponding compound in which X is OH with triphenylphosphine in the presence of either carbon tetrachloride or diethylazodicarboxylate.

In the cyclisation reaction, a base may be necessary. The base employed may be, for example, sodium or potassium hydroxide, sodium hydride, sodium carbonate, sodium hydride or lithium hydroxide. If X represents —S+(CH$_3$)R, then the base is suitably sodium carbonate or sodium hydride, or preferably lithium hydroxide. If X represents —O—P+Ph$_3$, no base is required.

The amino group in compound II may advantageously be protected with a suitable N-protecting group.

Suitable examples of N-protecting groups include those conventionally known for this use in peptide chemistry. Examples of such groups include carboxylic acid groups such as chloroacetyl, trifluoroacetyl, formyl, benzoyl, phthaloyl, phenylacetyl or pyridinecarbonyl; or acid groups derived from carbonic acid such as ethoxycarbonyl, benzyloxycarbonyl, t-butyloxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl or t-amyloxycarbonyl; or acid groups derived from sulphonic acid, e.g. p-toluenesulphonic acid; or other groups such as benzyl, trityl, o-nitrophenylsulphenyl, benzylidene or nitro.

Preferred N-protecting groups include t-butyloxycarbonyl and benzyloxycarbonyl.

The removal of the protecting group present in the resultant compound may be effected by an appropriate procedure depending upon the nature of the protective group. Typical procedures include hydrogenation in the presence of a palladium catalyst (e.g. palladium carbon or palladium black) for benzyloxycarbonyl, p-nitrobenzyloxycarbonyl, p-bromo-benzyloxycarbonyl, p-phenylazobenzyloxycarbonyl, p-(p'-methoxyphenylazo)benzyloxycarbonyl and trityl groups; treatment with hydrogen bromide in glacial acetic acid or trifluoroacetic acid for benzyloxycarbonyl, p-bromobenzyloxycarbonyl, p-phenylazobenzyloxycarbonyl and t-butyloxycarbonyl groups; and treatment with hydrochloric acid and/or acetic acid for trityl, t-butyloxycarbonyl, formyl and benzylidene groups.

The hydroxy group in compound II may also be protected by a group which may be removed after the reaction is complete.

The compounds of formula II may be prepared by methods analogous to those described in British Pat. No. 1,041,861. In the preparation of compound II, resolution may be carried out at any stage of the synthesis. Any suitable intermediate, or the racaemic form of compound II itself, may be resolved by conventional means.

A preferred precursor of the intermediate II is represented by structure III:

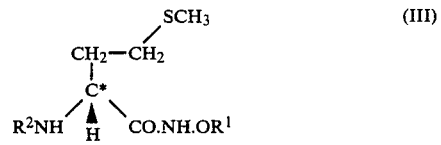

in which the carbon atom marked * is in the R configuration; wherein $R^1$ represents hydrogen or a hydroxy protecting group such as allyl, alkoxyalkyl, acyloxyalkyl, t-butyl or benzyl; and wherein $R^2$ represents a N-protecting group.

Compounds of formula III are novel and represent a further aspect of this invention. They may be prepared from D-methionine by reacting N-protected D-methionine of formula IV:

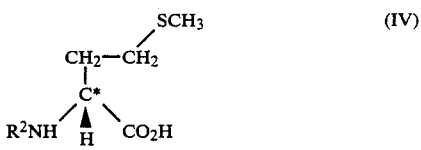

with an optionally O-protected hydroxylamine, $NH_2OR^1$.

Preferably $R^1$ represents benzyl or t-butyl, and $R^2$ represents benzyloxycarbonyl.

The invention also provides pharmaceutical compositions comprising the compound of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of the compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills or capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including polymeric acids and mixtures of polymeric acids with such materials as shellac, cetyl alcohol or cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil and peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone and gelatine.

In the treatment of neurodegeneration, a suitable dosage level is about 0.1 to 1000 mg/kg/day, preferably about 0.5 to 500 mg/kg/day and especially about 1 to 100 mg/kg/day. The compounds may be administered on a regimen of 1 to 4 times per day.

Biological Activity

A. Differentiation of properties between R(+) and S(−) isomers

Rotarod performance in mice

The rotarod test measures the ability of mice to maintain themselves on a rotating drum. This test is sensitive to drug induced muscle relaxation and ataxia.

Male Swiss Webster (SW) mice (18–20 g) or DBA/2 mice (8–12 g, 20–22 days) are trained to maintain themselves on a rotating drum (15 rev/min) for 120 seconds. Drugs dissolved in 0.9% NaCl injected in volume 10 ml/kg, intravenous in SW and i.p. in DBA/2. 15 minutes later latency to fall from rotarod is measured. Four doses of racemic HA-966, the R(+) isomer of this invention and the corresponding S(−) isomer were tested in independent groups of mice against vehicle treated controls with 8 animals in each group. Minimal effective doses, in mg/kg, to impair rotarod performance were as follows:

| Strain of mice | Racemic HA-966 | R (+) isomer of present invention | corresponding S (−) isomer |
|---|---|---|---|
| SW | 20 | 250 | 5 |
| DBA/2 | 25 | 250 | 10 |

These results demonstrate that in two strains of mice virtually all of the ataxic properties of HA-966 are present in the S(−) isomer whereas the undesirable ataxia is demonstrated by the compound of the present invention only at very high doses of 250 mg/kg.

Antagonism of audiogenic seizures in DBA/2 mice

Male DBA/2 mice (8–12 g) were exposed to a 125 dB and 14 kHz tone for 30 seconds, 15 minutes after administration (i.p.) of the test compounds. At least 4 doses of each compound were investigated against vehicle control in independent groups of 8 mice. Control mice received 0.9% NaCl. The number of mice not showing tonic seizures was noted. The results in terms of $ED_{50}$ values (i.e. the dose to protect 50% of the animals in mg/kg) are shown below:

| Racemic HA-966 | R (+) isomer of present invention | Corresponding S (−) isomer |
|---|---|---|
| 9.6 | 52.6 | 4.7 |

These results show that the ability to block seizures in mice genetically susceptible to intense sound resides in the R(+) isomer at doses which are totally devoid of sedative properties. By contrast, although the S(−) isomer shows anticonvulsant activity in this model, it is only at doses inducing marked sedation and ataxia.

Antagonism of NMDLA induced seizures

Male Swiss Webster mice were injected with N-methyl-DL-aspartic acid (NMDLA), 500 mg/kg s.c. Seizure and death were observed within 10 minutes. The test compounds were administered i.v. 15 minutes before NMDLA. At least 4 doses of each drug were evaluated against vehicle control and independent groups of 8 mice.

Protection was defined as absence of final tonic seizure during 30 minutes after NMDLA injection.

Results calculated as $ED_{50}$ (dose to protect 50% of mice in mg/kg) are shown below:

| Racemic HA-966 | R (+) isomer of this invention | Corresponding S (−) isomer |
|---|---|---|
| 1820.9 | 892.7 | >2000 |

These results demonstrate that the ability to block seizures induced with a selective agonist at the NMDA receptor resides totally in the R(+) isomer, with the S(−) isomer failing to show anticonvulsant activity even at doses producing marked sedation and eventually death (2000 mg/kg).

B. Demonstration of neuroprotection

The neuroprotective properties of the compound of this invention is demonstrated in the gerbil bilateral carotid occlusion model.

Gerbils are anaesthetised (12% isoflurane, 70% nitrous oxide and 30% oxygen). The carotid arteries are isolated and clips placed on them for 5 minutes. After surgical closure the animals survive for 4 days, and are perfusion fixed. The brains are removed for histological processing. 40 μm frozen sections are stained with cresyl violet. The area of neuronal degeneration at the level of the hippocampus is quantified using an image analyser (Gill, Foster and Woodruff, J. Neurosci., 1987, 7, 3343).

Untreated animals receiving a 5 minute period of ischaemia served as controls (10 per group).

In this model the R(+) isomer of the present invention demonstrated histological neuroprotection when administered at 10 mg/kg i.p. during the period of occlusion.

The (−) isomer, (3S)-3-amino-1-hydroxypyrrolidin-2-one, was prepared, in order to provide the comparison shown above, by the following procedures:

Preparation I (a) t-Butoxycarbonyl-L-methionyl-O-benzylhydroxamate was prepared in an analogous manner to the preparation of the D-enantiomer described in Example 1(b) below on a 0.221 mol scale from commercially available Boc-L-Met (yield 96%).

(b) (3S)-3-t-butoxycarbonylamino-1-benzyloxypyrrolidin-2-one was prepared from t-butoxy-carbonyl-L-methionyl-O-benzylhydroxamate above in an analogous manner to the preparation of the -D-enantiomer described in Example 1(c) below. Isolation after silica gel chromatography and recrystallisation yielded the title compound in 37.1% yield, mp 113°–114° C., $[α]_D$ −54.2° (c=1%, MeOH). $^1$H NMR identical with that described in Example 1(c) below.

(c) Preparation of (3S) 3-amino-1-hydroxypyrrolidin-2-one (3S)-3-Butoxycarbonylamino-1-benzyloxypyrrolidin-2-one (from (b) above, 5 g, 49 mmol) was dissolved in trifluoroacetic acid (80 ml) and after 15 mins the solution was evaporated and diethyl ether (200 ml) added. The crystalline solid was removed by filtration and dissolved in 50% aqueous ethanol (200 ml), and the solution hydrogenated in the presence of palladium black (0.8 g) for 2 h at 50 psi. The catalyst was removed by filtration, the solution was evaporated and the residue dissolved in propan-2-ol, then concentrated ammonia solution added to give pH 7.5. On standing at +5° C. crystals formed which were removed by filtration, dried, and recrystallised from aqueous ethanol to yield the title compound (4.47 g, 78.6%) mp=166° C. $[\alpha]_D$ −106.1° (c=1%, $H_2O$). $^1$H NMR was identical with that described in Example 1(e) below.

The following Examples illustrate the preparation of compounds of this invention.

EXAMPLE 1

(3R)-3-Amino-1-hydroxypyrrolidin-2-one (a) Preparation of t-butoxycarbonyl-D-methionine D-Methionine (50.3 g, 0.34 mol) was dissolved in water (700 ml) containing sodium carbonate (71.5 g, 0.675 mol). To this solution was added a solution of di-tert-butyl dicarbonate (81.0 g, 0.37 mol) in dioxan (250 ml) and the mixture left stirring for 16 h at room temperature. Water (1.5l) was added and the solution was washed twice with diethyl ether. The aqueous phase was acidified to pH 3 by addition of solid citric acid and the product extracted three times with ethyl acetate (500 ml). The combined organic phases were washed successively twice with water, once with saturated brine, then were dried over magnesium sulfate. Evaporation gave t-butoxycarbonyl-D-methionine as an oil (87.6 g, 100%). $[\alpha]_D$ +19.0° (c=1%, MeOH).

(b) Preparation of t-butoxycarbonyl-D-methionyl-O-benzylhydroxamate

A solution of t-butoxycarbonyl-D-methionine (Example 1(a), 4.4 g, 17.65 mmol) in anhydrous THF (30 ml) was cooled to −20° C. under an atmosphere of dry nitrogen. N-Methylmorpholine (1.94 ml, 17.65 mmol) and isobutylchloroformate (2.31 ml, 17.65 mmol) were added and the solution was kept between −15° C. and −20° C. for 15 mins. A mixture of O-benzylhydroxylamine hydrochloride (2.82 g, 17.67 mmol) and N-methylmorpholine (2.34 ml, 21.3 mmol) in THF (20 ml) was added and the solution was then kept at −15° C. for 30 min then allowed to warm slowly to ambient temperature. After 16 h the solvent was removed by evaporation and the residue was partitioned between ethyl acetate and water. The organic phase was washed successively with 5% aqueous sodium bicarbonate, water, 10% aqueous citric acid, water, saturated brine. After drying over $Na_2SO_4$, the ethyl acetate was removed in vacuo to give 6.04 g (96.8%) of the title compound as a crystalline solid mp=92°–93° C. $^1$H NMD α ($CDCl_3$) 9.21 (1H, broad s; NHO), 7.40-7.26 (5H, m, phenyl), 5.20 (1H, d, J=8.4 Hz, NH-CH), 4.90 (2H, s, $OCH_2$), 4.13 (1H, m, NH—CH), 2.55—2.47 (2H, m, $CH_2S$), 2.09-1.80 (5H, m, S—$CH_3$ and CH—$CH_2$—$CH_2$), 1.42 (9H, s, $C(CH_3)_3$). m/e (CI+) 355 (M+1), (CI−) 353 (M−1) $[\alpha]_D$+38.6 (c=1%, MeOH).

(c) Preparation of (3R)-3-t-butoxycarbonylamino-1-benzyloxypyrrolidin-2-one t-Butoxycarbonyl-D-methionyl-O-benzylhydroxamate (Example 1(b), 73 g, 0.206 mol) was dissolved in methanol (1.5l) and to this solution was added a solution of LiOH, $H_2O$ (8.64 g, 0.202 mol) in methanol (200 ml), and benzyl bromide (40.51 g, 0.237 mol). The solution was heated at 60° C. for 1 h and further benzyl bromide (10.1 g, 0.059 mol) added. After heating at 60° C. for a further 3 h the solution was cooled to ambient temperature over 12 h, then was evaporated. The residue was partitioned between ethyl acetate (300 ml) and water (100 ml) (with brine added to prevent emulsification). The organic phase was dried over $Na_2SO_4$, the solution concentrated in vacuo and the residue filtered through silica gel (422 g, 230–400 Mesh) eluting with ethyl acetate/hexane (1:1) to give the crude product (40.7 g). This was recrystallised from ethyl acetate/hexane to yield the title compound (19.44 g, 30.8%), mp 113°–114° C. $[\alpha]_D$= +56.8° (c=1%, MeOH). $^1$H NMR δ ($CDCl_3$) 7.44−7.26 (5H, m, phenyl), 5.05−4.96 (3H, dd+broad s, Jgem=11.00 Hz, —$OCH_2$+CONH), 4.09 (1H, m, NHCH—$CH_2$), 3.24−3.20 (2H, m, $CH_2$—N), 2.49 (1H, m, —CH—$CH_AH_B$), 1.84−1.72 (1H, m, —CH—$CH_AH_B$), 1.46 (9H, s, $C(CH_3)_3$). m/e (CI+) 307 (M+1), (CI−) 305 (M-1).

(d) Preparation of (3R)-3-amino-1-benzyloxypyrrolidin-2-one trifluoroacetate salt (3R)-3-t-Butoxycarbonylamino-1-benzyloxypyrrolidin-2-one (Example 1(c), 19.02 g, 62.2 mmol) was dissolved in trifluoracetic acid (150 ml). After 15 mins the solution was evaporated and the residue was crystallised from diethyl ether to give the title compound (20.31 g, 100%). mp=185° C. $[\alpha]_D$= +41.4° (c=1% MeOH), $^1$H NMR δ ($D_2O$) 7.52−7.48 (5H, m, phenyl), 5.04 (2H, s, $OCH_2$), 4.13 (1H, t, J=9.26 Hz, αCH—$CH_2$), 3.63−3.59 (2H, m, $CH_2$—N), 2.61−2.57 (1H, m, —CH—$CH_A$—$H_B$), 2.13−2.02 (1H, m, —CH—$CH_AH_B$). m/e (FAB+) 207 (M+1); (FAB−) 205 (M-1).

(e) Preparation of (3R)-3-amino-1-hydroxypyrrolidin-2-one (3R)-Amino-1-benzyloxypyrrolidin-2-one trifluoracetate (Example 1(d), 19.24 g, 60.3 mmol) was hydrogenated with palladium black (800 mgs) in 50% aqueous ethanol (240 ml) at 50 psi for 2.5 h. The solution was filtered and evaporated to dryness. To the residue was added ethanol (70 ml) and sufficient concentrated aqueous ammonia to give pH 7.5. On cooling to +5° C., a solid deposited which was recrystallised from $H_2O$/EtOH (1:4) to give the title compound (5.8 g, 82.5%), mp 167° C. $[\alpha]_D$ +104.5 (c=1%, $H_2O$), $^1$H NMR δ ($D_2O$) 3.92 (1H, t, J=8.5 Hz, N—CH—$CH_2$), 3.63−3.59 (2H, m, $CH_2$—N), 2.57−2.48 (1H, m, —CH—$CH_AHB$), 1.99−1.89 (1H, m, —CH—$CH_AH_B$), m/e (CI+) 117 (m+1), (CI−) 115 (m-1).

EXAMPLE 2

(3R)-3-amino-1-hydroxypyrrolidin-2-one

(a) Preparation of t-butoxycarbonyl-D-methionylhydroxamate t-Butoxycarbonyl-D-methionine (20 g, 80.22 mmol) is added to a solution of pentachlorophenol (21.37 g) and dicyclohexylcarbodiimide (16.55 g, 80.3 mmol) in ethyl acetate (200 ml). After 2.5 h the solution is filtered after 2.5 h and the filtrate evaporated to dryness. The residue is recrystallised from hot methanol to give t-butoxycarbonyl-D-methionine pentachlorophenyl ester (32.5 g, 81.4%). A sample of this material (1.03 g, 2.14 mmol) is dissolved in DMF (10 ml) and to this solution is added hydroxylamine hydrochloride (0.149 g, 2.16 mmol) and diisopropylethylamine (0.91 ml, 5.2 mmol). After 16 h at room temperature the solvent is removed by evaporation and the residue partitioned between diethyl ether and 5% aqueous sodium carbonate. The aqueous phase (together with an insoluble oil which forms at the interface) is acidified by addition of citric acid to pH 6 and the product extracted twice with ethyl acetate. The combined ethyl acetate phases are washed successively with water and brine then dried over sodium sulfate. After the solvent is removed by evaporation the product is obtained as a crystalline solid by addition of a small amount of diethyl ether. A sample is recrystallised from ethyl acetate/hexane. mp 133°–134° C. $^1$H NMR $\delta$ (CDCl$_3$) 8.50 (1H, broad s, —NH—), 5.58 (1H, m, urethane NH), 4.23 (1H, m, $\alpha$—CH), 2.56 (H, m, $\gamma$CH$_2$), 2.09 (3H, s, S—CH$_3$), 2.03 (1H, m, CH—CH$_A$H$_B$), 1.91 (1H, m, CH—CH$_A$H$_B$), 1.43 (9H, s, C(CH$_3$)$_3$); m/e (EI+) 265 (M+1), (CI−) 2.63 (M−1).

(b) Preparation of (3R)-3-amino-1-hydroxypyrrolidin-2-one

To a solution of t-butoxycarbonyl-D-methionylhydroxamate (Example 2(a), 4.62 g, 18.5 mmol) in methanol (50 ml) is added sodium carbonate (3.917 g) and benzyl bromide (4.4 ml), and the solution is left at ambient temperature for 16 h. The solvent is removed by evaporation and the residue is filtered through silica gel using ethyl acetate/petroleum ether (1:1) to give (3R)-3-t-butoxycarbonylamino-1-benzyloxy-pyrrolidin-2-one (1.75 g, 30.9%). A sample of this is then deprotected as described in Example 1(d) and Example 1(e) to yield the title compound (194 mg, overall yield 8.3%). Characterising data is identical with that described in Example 1(e).

EXAMPLE 3

(3R)-Amino-1-hydroxypyrrolidin-2-one

(a) Preparation of bis-N,O-(t-butoxycarbonyl-L-phenylalanyl)-3-amino-1-oxypyrrolidin-2-one A solution of Boc-L-Phe (10.72 g, 40.4 mmol) in DMF (50 ml) was cooled to 0° C. and to this was added a solution of DCC (8.24 g, 40 mmol) in DMF (10 ml). (±)3-Amino-1-hydroxypyrrolidin-2-one (2.32 g, 20 mmol) was added and the solution maintained at 0° C. for 6.5 h. The solution was filtered and evaporated to dryness, then diethyl ether (55 ml) added and the solution was allowed to stand at +5° C. for 16 h. The crystals which formed were removed by filtration, washed with diethyl ether and dried to yield 2.65 g (21.7%) of the pure diastereomer A, (3R)-bis-N,O-(t-butoxycarbonyl-L-phenylalanyl)-3-amino-1-oxypyrrolidin-2-one, mp 174°–175° C. $^1$H NMR (CDCl$_3$) 7.34−7.20 (10H, m, phenyl), 6.47 (1H, d, J=6.8 Hz, amide NH), 5.03 (1H, d, J=7.57 Hz urethane —NH), 4.93 (1H, d, J=7.68 Hz, urethane NH), 4.71 (1H, m, $\alpha$CH, Phe$^1$), 4.51 (1H, m, $\alpha$CH, lactam), 4.41 (1H, m, $\alpha$CH, Phe$^2$), 3.54 (2H, m, $\delta$CH$_2$ lactam, 3.22 (2H, m, $\beta$CH$_2$, Phe$^1$), 3.11 (2H, m, $\beta$CH$_2$, Phe$^2$), 2.63 (1H, m, CH—CH$_A$H$_B$, lactam), 1.87 (1H, m, CH—CH$_A$H$_B$, lactam), 1.39+1.38 (18H, s+s, C(CH$_3$)$_3$, BocPhe$^1$+C(CH$_3$)$_3$, BocPhe$^2$). A further crop (1.23 g, 10.1%) of this material could be obtained from the mother liquor by fractional crystallisation using DMF/diethyl ether. Purification of the mother liquors by flash chromatography using ethyl acetate/hexane (1:1), followed by repeated crystallisation from ethyl acetate at (5° C. to remove remaining diastereomer A) gave the more soluble diastereomer B (3S)-bis-N,O-(N-t-butoxycarbonyl-L-phenylalanyl)-3-amino-1-oxypyrrolidin-2-one from the mother liquor by precipitation with hexane (1.82 g, 14.9%). The diastereomeric purity of each isomer was found to be >95% by $^1$H NMR.

(b) Preparation of (3R)-N-(t-butoxycarbonyl-L-phenylalanyl)-3-aminohydroxypyrrolidin-2-one Diastereomer A (Example 3(a), 1.41 g, 2.31 mmol) was dissolved in methanol (10 ml) by addition of N,N-dimethylethylenediamine. After 40 mins the methanol was removed by evaporation and the residue partitioned between ethyl acetate and 10% citric acid solution. The organic phase was washed twice with water, then with brine and dried over Na$_2$SO$_4$. After evaporation of the ethyl acetate, diethyl ether was added to the residue to give the title compound (0.763 mg, 90.9%). m/e (FAB+) 364 (M+1), (FAB−) 362 (M−1).

(c) Preparation of (3R)-3-amino-1-hydroxypyrrolidin-2-one (3R)-N-(Butoxycarbonyl-L-phenylalanyl)-3-aminohydroxypyrrolidin-2-one (Example 3(b), 712.3 mg, 1.96 mmol) was dissolved in anhydrous trifluoroacetic acid (10 ml) and after 30 mins the solution was evaporated to dryness. The residue was treated with diethyl ether to give a hygroscopic solid, (3R)-3-(L-phenylalanyl)-amino-1-hydroxypyrrolidin-2-one trifluoroacetate salt (780 mg). $^1$H NMR $\delta$ (D$_2$O) 7.44−7.27 (5H, m, phenyl), 4.85 (1H, t, J=9.2 Hz $\alpha$CH), 4.19−4.15 (1H, dd, $\alpha$CH$_2$), 3.58−3.51 (2H, m, $\gamma$CH$_2$—N), 3.25 and 3.14 (2H, m, $\beta$CH$_2$Ph), 2.37−2.29 (1H, m, CH—CH$_A$H$_B$), 1.59−1.48 (1H, m, CH—CH$_A$H$_B$); m/e FAB+(M+1)=264.

This salt (719.4 mg) was dissolved in ethanol (35 ml) and to the solution was added diisopropylethylamine (0.705 ml, 4.05 mmol) and phenylisothiocyanate (0.543 ml, 4.54 mmmol). After 45 mins the solution was evaporated to dryness and to the residue was added trifluoroacetic acid (20 ml). The solution was warmed to 40° C. and then allowed to stand at room temperature for 30 min. The solvent was removed by evaporation and water (20 ml) and diethyl either (20 ml) were added. The aqueous phase was applied to a column containing Dowex 50W X8 (H+ form, 6.28 ml, 200–400 mesh) and after washing the resin with water (30 ml), the product was eluted using dilute aqueous ammonia. Crystallisation from ethanol gave the title compound (135.2 mg, 64.5%), mp 164° C. [$\alpha$]$_D$+101° (c=0.5%, H$_2$O). $^1$H NMR δ (D₂O) identical with that described in Example 1(e). m/e (EI+) 117 (M+1), (EI−) 115 (M−1).

What is claimed is:

1. R(+)-3-Amino-1-hydroxypyrrolidin-2-one of formula I:

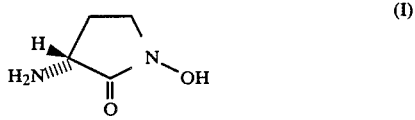

or a pharmaceutically acceptable acid addition salt thereof.

2. A mixture of the R(+) and S(−) isomers of 3-amino-1-hydroxypyrrolidin-2-one comprising at least 99% of the R(+) isomer.

3. A pharmaceutical composition comprising an effective amount of R(+)-3-amino-1-hydroxypyrrolidin-2-one or a pharmaceutically acceptable acid addition salt thereof together with a pharmaceutically acceptable carrier or excipient.

4. The method for the treatment and/or prevention of convulsions which comprises administering to a patient in need of such treatment an effective amount of R(+)-3-amino-1-hydroxypyrrolidin-2-one or a pharmaceutically acceptable acid addition salt thereof.

5. A method for the treatment and/or prevention of neurodegenerative disorders which comprises administering to a patient in need of such treatment an effective amount of R(+)-3-amino-1-hydroxypyrroldin-2-one or a pharmaceutically acceptable acid addition salt thereof.

* * * * *

UNITED STATES PATENT AND TRADEMARK OFFICE
CERTIFICATE OF CORRECTION

PATENT NO. : 4,863 953
DATED : September 5, 1989
INVENTOR(S) : P.D. Leeson et al It is certified that error appears in the above-identified patent and that said Letters Patent is hereby corrected as shown below:

On the title page assignee should read

---(73) Assignee: Merck Sharp & Dohme Limited---.

Signed and Sealed this

Twenty-second Day of May, 1990

*Attest:*

HARRY F. MANBECK, JR.

*Attesting Officer*  *Commissioner of Patents and Trademarks*